United States Patent [19]

Focht

[11] Patent Number: 5,552,321

[45] Date of Patent: Sep. 3, 1996

[54] TEMPERATURE CONTROLLED CULTURE DISH APPARATUS

[75] Inventor: Daniel C. Focht, Butler, Pa.

[73] Assignee: Bioptechs Inc., Butler, Pa.

[21] Appl. No.: 111,107

[22] Filed: Aug. 24, 1993

[51] Int. Cl.⁶ .................................................. C12M 1/38
[52] U.S. Cl. ...................... 435/286.1; 435/808; 435/809; 359/395
[58] Field of Search ...................... 435/284, 285, 435/287, 289, 290, 296–298, 299, 301, 316, 808, 809; 422/99, 102, 104; 359/391, 395, 396–398; 219/429, 432, 435

[56] References Cited

U.S. PATENT DOCUMENTS

| | | | |
|---|---|---|---|
| 2,440,472 | 4/1948 | Horner et al. | 359/395 |
| 3,745,091 | 7/1973 | McCormick | 435/301 |
| 3,883,398 | 5/1975 | Ono | 435/301 |
| 4,299,920 | 11/1981 | Peters | 435/284 |
| 4,301,252 | 11/1981 | Baker et al. | 435/290 |
| 4,674,846 | 6/1987 | Lippman | 359/395 |
| 4,888,463 | 12/1989 | Middlebrook | 359/395 |
| 5,019,691 | 5/1991 | Lai | 219/432 |
| 5,134,070 | 7/1992 | Casnig | 435/297 |
| 5,170,286 | 12/1992 | Zimmerberg et al. | 359/395 |

FOREIGN PATENT DOCUMENTS

| | | | |
|---|---|---|---|
| 3511165 | 10/1985 | Germany | 359/395 |
| 3208819 | 8/1988 | Japan | 359/396 |
| 0358682 | 11/1972 | U.S.S.R. | 359/395 |
| 8703703 | 6/1987 | WIPO | 359/395 |

OTHER PUBLICATIONS

Steier "Heated Microscope Stage: A Temperature Control for Live–Cell Microscopy", Laboratory Practice, vol. 24, No. 6 (1975) p. 417.

*Primary Examiner*—William H. Beisner

[57] ABSTRACT

A temperature controlled culture dish apparatus is disclosed. The apparatus consists of a culture dish assembly, a stage insert assembly, and a temperature controller. The culture dish assembly has a culture dish bottom which is manufactured from glass of high optical transmissivity coated with a transparent electrically conductive material. The biological specimen is grown directly on the culture dish bottom. The culture dish assembly is then placed into a recess in the stage insert assembly for microscopic examination. The biological specimen is not disrupted or transferred from the culture dish in which it was grown for purposes of examination. Power wires on the floor of the recess in the stage insert assembly contact bus bars on the transparent electrically conductive coating material. A thermistor on the floor of the recess in the stage insert assembly contacts the bottom of the culture dish bottom. Electrical leadouts to a temperature controller then enable the temperature controller circuitry to provide appropriate voltages to the power wires, thereby maintaining the culture dish bottom and the biological specimen at a constant temperature.

3 Claims, 2 Drawing Sheets

1

TEMPERATURE CONTROLLED CULTURE DISH APPARATUS

BACKGROUND OF THE INVENTION

1. Field of the Invention

The invention relates to an apparatus for microscopic examination of biological specimens with precise control of the temperature of the specimen.

2. Prior Art

In the biological sciences, it has been a longstanding problem to maintain satisfactory control of the temperature at which a biological specimen is examined under a microscope.

The biological specimen is usually grown in a standard laboratory culture dish manufactured from a plastic. The biological specimen may be observed by microscope in the culture dish provided the microscope is set for low magnification and the viewing period is short. For longer viewing periods, however, it is necessary to maintain the specimen at a constant, controlled temperature. For higher magnification, it is necessary that the specimen be mounted on a surface of high optical transmissivity which is sufficiently thin to permit the use of high numeric aperture objective lenses.

Microscopic examination of the biological specimen at high magnification (400× or greater, for example) with a constant, controlled temperature has presented problems not resolved until the present invention.

If the specimen is to be viewed in the culture dish in which it was grown but at high magnification, then the standard plastic laboratory culture dish is not acceptable because the thickness of the plastic prevents the use of high numeric aperture objective lenses. Furthermore, where the microscopic viewing technique requires polarization of light, then a plastic culture dish is not acceptable as plastic will depolarize light.

In addition, plastic does not conduct heat well, resulting in long thermal time ratios which prevent the precise control of temperature necessary.

If the specimen is first removed from the culture dish and placed into some other apparatus appropriate for use with high numeric aperture objective lenses, then the biological specimen may be damaged. Furthermore, removal of the specimen from the culture dish in which it was grown to a viewing apparatus is time consuming. Even when the specimen is removed from the culture dish and placed into some other apparatus, there still remains the problem of placing the apparatus onto a heating device with sufficient control of heat transfer and measurement of temperature to assure precise temperature control.

There have been prior systems which enable the scientist to view the biological specimen with temperature control on the surface on which the specimen was grown. Such systems generally require that the culture dish itself be placed onto a stage which is electrically heated. The heat from the stage then transfers by conduction to the culture dish and then to the specimen. Such systems, while operable, generally feature imprecise temperature control with slow temperature stabilization. When perfusion liquids are added to the sample, temperature drops occur from which these systems are slow to recover.

These problems are solved by the present invention.

SUMMARY OF THE INVENTION

The present invention achieves the object of precise control of specimen temperature during microscopic examination without disruption or damage to the biological specimen. The temperature controlled culture dish apparatus achieves this goal by dividing the apparatus into a culture dish assembly and a stage insert assembly. The bottom dish of the culture dish is manufactured from glass of high optical transmissivity which is coated with a transpart electrically conductive material, such as but not limited to indium tinoxide ("ITO"). The biological specimen is grown directly on that bottom dish. The culture dish assembly is then inserted into a recess in the stage insert assembly for microscopic viewing. There is no disruption or need to remove the biological specimen from one container to another in preparation for microscopic examination. Power wires mounted on the floor of the insert recess come into contact with bus bars on the bottom side of the culture dish bottom. A voltage, controlled by a temperature controller, is then applied, causing an electrical current to flow through the ITO coating, thereby heating the glass of the culture dish bottom itself. A thermistor mounted on the floor of the recess in the stage insert assembly comes into contact with the ITO coating, thereby providing a temperature measurement which is sent to the temperature controller circuitry. Because the apparatus heats directly the very glass on which the specimen rests and because the thermistor measures temperature directly from the very glass on which the specimen rests, precise control of temperature with rapid corrections for deviation is achieved.

After the microscopic examination has been completed, the biological specimen and the culture dish assembly can be returned to the incubator and preserved for further viewing. Or, the culture dish assembly and specimen can be discarded, leaving the stage insert assembly ready to accept the insertion of another culture dish assembly.

DESCRIPTION OF THE PREFERRED EMBODIMENT

Figure 1:
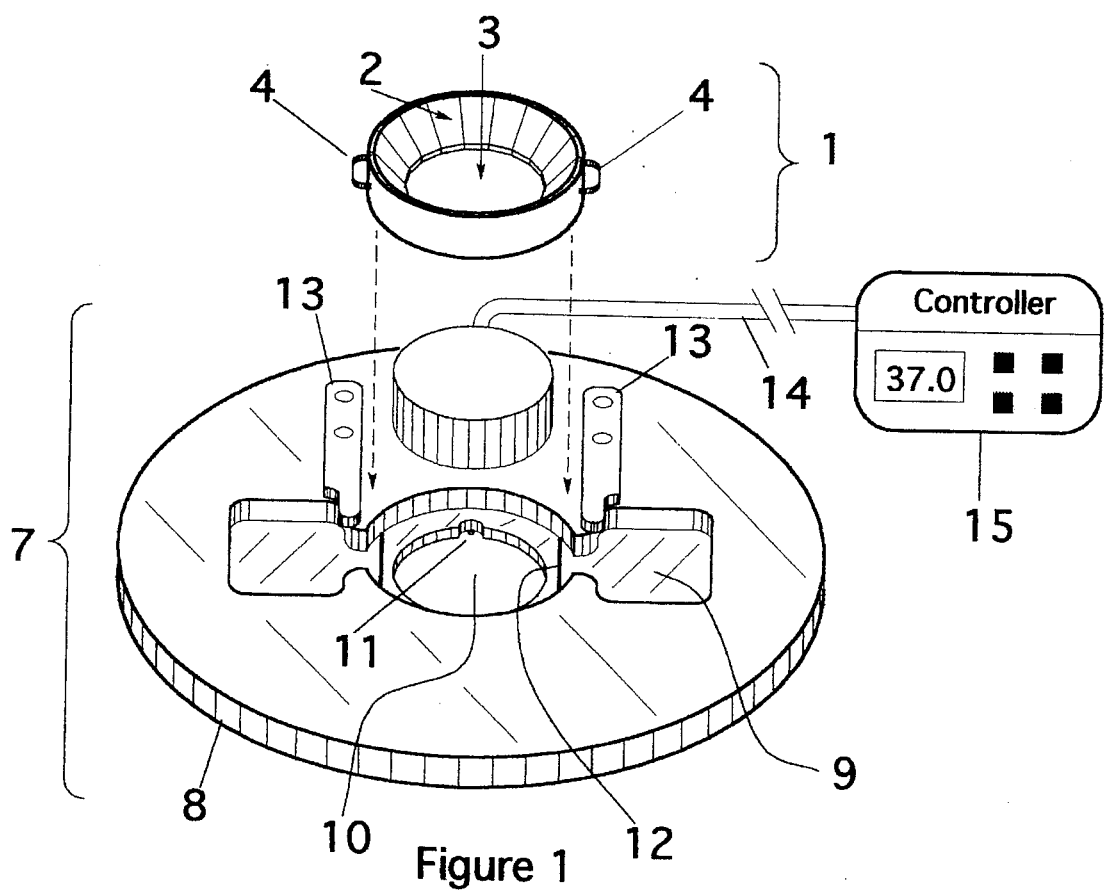
FIG. 1 is a perspective view of the temperature controlled culture dish apparatus and depicts both the culture dish, the stage insert assembly, and the temperature controller.
Figure 2:
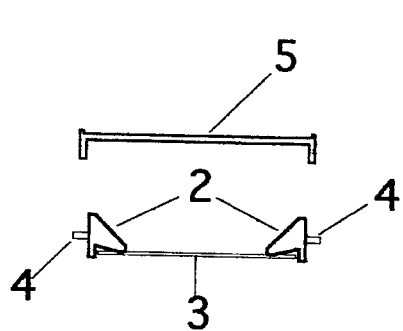
FIG. 2 is a section view from the side of the culture dish assembly.

A temperature controlled culture dish apparatus according to the preferred embodiment of the present invention is shown in perspective in FIG. 1. The culture dish assembly 1 is shown elevated above the stage insert assembly 7. In actual operation, however, the culture dish assembly 1 is lowered into a recess 9 in the stage insert assembly 7. The condenser lens of an inverted microscope is then brought into position above the apparatus and the objective lens of the microscope is positioned below the circular cutout be of the stage insert 8. Although an inverted microscope is most commonly utilized in this application, an upright microscope may also be utilized. The investigator may then view the biological specimen located on the upper surface of the culture dish bottom. The temperature of that biological specimen is precisely controlled by the invention.

The culture dish assembly 1 is comprised of: the molded ring mount 2, the culture dish bottom 3, a plurality of alignment tabs 4, a cover 5, and two bus bars 6. The culture dish bottom is manufactured of glass with high optical transmissivity. The bottom side of the glass is coated with a transparent electrically conductive coating material. In the preferred embodiment, that material is indium tinoxide ("ITO"), but there are a number of transparent electrically conductive materials which could be utilized. It is a physical property of such electrically conductive materials that when a direct current voltage is applied at two points on the coating, an electrical current flows through the coating, causing the coating to release heat. Heat from the coating is then used to achieve and maintain a desired temperature in the biological specimen under microscopic examination.

The culture dish bottom 3 is bonded or cemented into a rabbeted recess in the molded ring mount 2. The rabbet is appropriately dimensioned with respect to the thickness of the culture dish bottom such that the culture dish assembly, when placed on a flat surface, will rest on the lower surfaces of the molded ring mount 2 and without contact between the culture dish bottom 3 and the surface.

The molded ring mount 2 has attached appropriately located and dimensioned alignment tabs 4 the function of which is to orient the culture dish assembly when it is lowered into the recess 9 in the stage insert 8.

The molded ring mount 2 may be but need not be manufactured with tapered or sloped sides to maximize free area above the culture dish bottom 3 to accommodate the placement of probes, perfusion tubes, or other instruments and to minimize the fluid volume at the optical aperture at the dish bottom.

Figure 3:
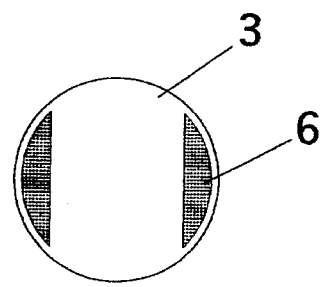
FIG. 3 is a planview of the underside of the culture dish bottom.
Figure 4:
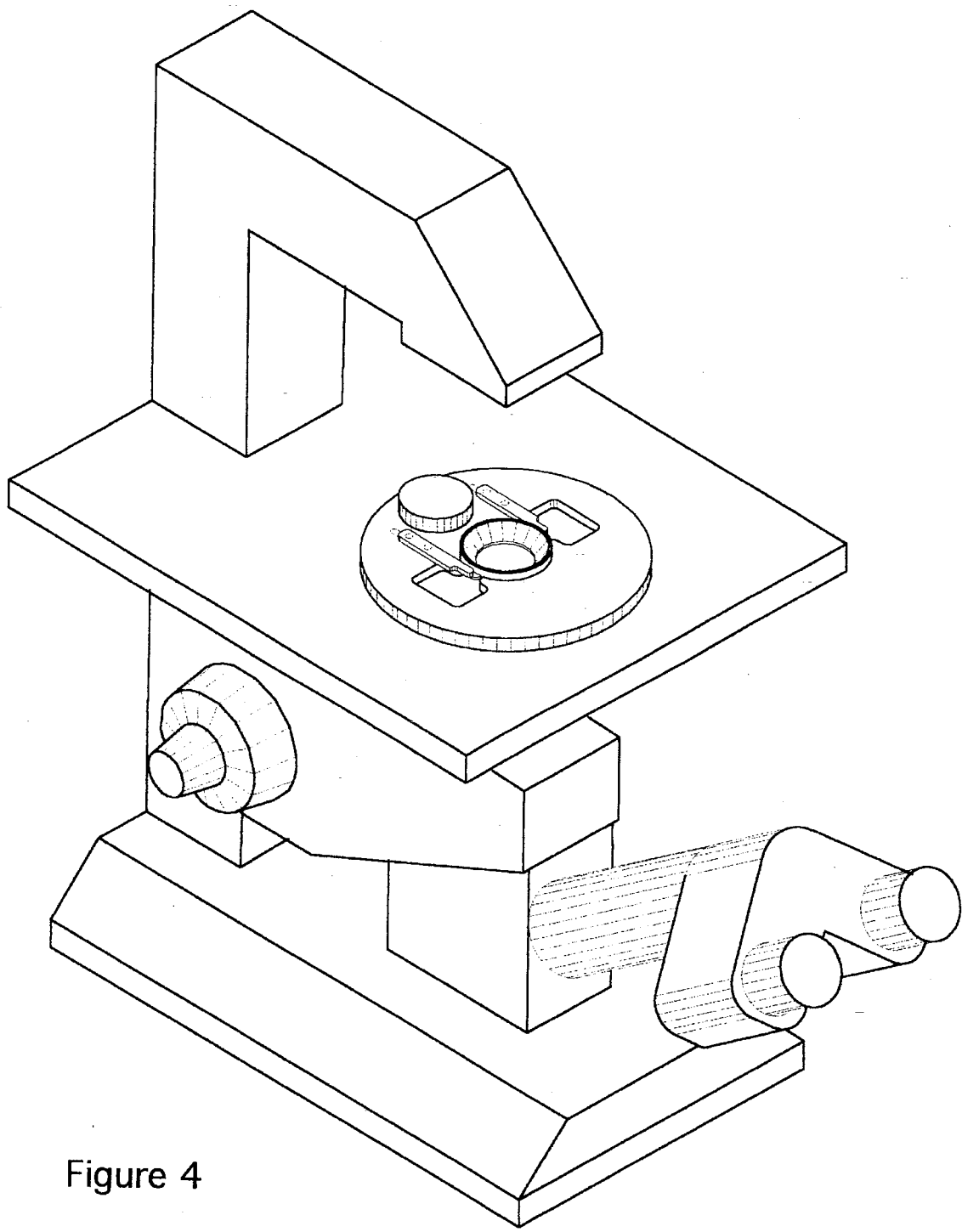
FIG. 4 is a perspective drawing which depicts the temperature controlled culture dish apparatus in operation on the viewing stage of a microscope.

The bottom side of the culture dish bottom 3, as shown by FIG. 3, is coated with a electrically conductive substance at two opposing segments, thereby forming two bus bars 6. These bus bars may be formed from any appropriate conductive material, such as silver-embedded epoxy applied via the silk screen process. The purpose of the bus bars 6 is to provide an area of solid electrical contact between the ITO coating on the bottom of the culture dish bottom 3 and the bus bar power wires 12 of the stage insert assembly 7.

The stage insert assembly consists of: the stage insert 8; a recess 9; a circular cutout 10; a thermistor 11, power wires 12; retaining tabs 13; necessary electrical wiring and electrical leadouts 14.

The electrical leadouts 14 are connected through appropriate connectors to a temperature controller 15, which applies appropriate voltages to the bus bar power wires 12, as determined by the temperature controller's 15 circuitry. A thermistor 11 in contact with the ITO measures the temperature of the ITO coating and provides that temperature measurement as an input to the temperature controller The temperature controlled culture dish apparatus operates as follows:

The biological specimen is cultured or grown directly in the culture dish assembly in the same manner as with any non-temperature controlled culture dish. A cover 5 is provided for use during the culture phase to protect the specimen from contamination. The cover may be but need not be removed prior to microscopic examination of the biological specimen. Prior to microscopic examination, the culture dish assembly 1 is placed into the stage insert assembly 7, the alignment tabs 4 assuring proper orientation of the culture dish assembly 1 in the recess 9 of the stage insert 8. The retaining tabs 13 are then pivoted (if mounted on a pivot mounting) or slideably moved (if mounted on a slide mounting) to lock the culture dish assembly 1 into position. The bus bar power wires 12 come into direct contact with the bus bars 6 on the bottom side of the culture dish bottom 3. The thermistor 11 comes into direct contact with the ITO coating of the culture dish bottom 3. The electrical leadouts 14 are then connected to the temperature controller 15. The operator then selects a desired temperature on the controls of the temperature controller 15, and the temperature controller 15 adjusts the DC voltage applied across the bus bars 6 in such a manner as to control the temperature of the ITO coating of the culture dish bottom 3, and hence of the biological specimen to be microscopically examined.

A specific embodiment of the present invention has been described in detail herein, and it will be appreciated by those skilled in the art that various modifications and alternatives to the embodiments could be developed in light of the overall technique of the disclosure. For example, the materials from which the stage insert 8 and the molded ring mount 2 are manufactured could be altered or modified, or the shape of the recess 9 in the stage insert 8 and of the alignment tabs 4 could be altered or modified. The culture dish bottom 3 could be manufactured from various thicknesses of glass, and the shape of the molded ring mount 2 could be altered according to the needs of the user. None of these changes would materially vary the invention, and all would be equivalents to the preferred embodiment herein disclosed. Accordingly, the particular arrangements are illustrative only and are not limiting as to the scope of the present invention which is given the full breadth of the appended claims and any and all equivalents thereof.

What is claimed is:

1. An apparatus for viewing a biological specimen through a microscope with precise control of specimen temperature, comprising:

(a) a culture dish assembly consisting of:
 (i) a dish bottom of glass with high optical transmissivity;
 (ii) a transparent electrically conductive coating material on the underside of the dish bottom;
 (iii) electrically conductive bus bars attached to the transparent electrically conductive coating material at a plurality of locations;
 (iv) a molded ring mount attached to the dish bottom the sides of which molded ring mount cause the culture dish assembly to take the form of a cylinder and defines an optical aperture of the dish bottom;

(b) a stage insert assembly consisting of:
 (i) a stage insert containing a recess dimensioned to accept the culture dish assembly;
 (ii) a circular cutout in the stage insert to permit unobstructed microscopic viewing through the optical aperture existing at the culture dish bottom;
 (iii) power wires on the recess in the stage insert which power wires come into contact with the bus bars on the transparent electrically conducive coating material on the culture dish bottom;
 (iv) a thermistor on the recess in the stage insert which comes into contact with the transparent electrically conductive coating material on the culture dish bottom and which measures the temperature of the culture dish bottom and communicates that temperature to a temperature controlling means;

(c) temperature controlling means which regulates the electrical voltage placed on the power wires, thereby regulating the heat given off by the transparent electrically conductive coating material, and thereby regulating the temperature of the biological specimen on the surface of the culture dish bottom.

2. The controlled temperature culture dish apparatus of claim 1 wherein the culture dish assembly has alignment tabs which fit into recesses in the stage insert assembly, thereby assuring proper alignment of the power wires and the bus bars on the transparent electrically conductive coating material of the culture dish bottom.

3. The controlled temperature culture dish apparatus of claim 1 wherein the sides of the molded ring mount of the culture dish assembly are tapered to maximize free space above the culture dish bottom and minimize fluid volume at the optical aperture at the circular cutout in the stage insert.

* * * * *